United States Patent [19]

Ackerman et al.

[11] Patent Number: 4,861,783

[45] Date of Patent: Aug. 29, 1989

[54] 4-QUINOLINE CARBOXYLIC ACID DERIVATIVES USEFUL FOR TREATING SKIN AND MUCO-EPITHELIAL DISEASES

[75] Inventors: Neil R. Ackerman, Greenville; Richard R. Harris, Wilmington; Scott E. Loveless, Newark, all of Del.; Russel H. Neubauer, West Chester, Pa.

[73] Assignee: E. I. Du Pont de Nemours and Company, Wilmington, Del.

[21] Appl. No.: 186,242

[22] Filed: Apr. 26, 1988

[51] Int. Cl.$^4$ ............................................. A61K 31/47
[52] U.S. Cl. ..................................... 514/311; 514/171; 514/314; 514/861; 514/863
[58] Field of Search ............... 514/311, 314, 171, 861, 514/863

[56]  References Cited

U.S. PATENT DOCUMENTS 4,680,299  7/1987  Hesson ................................. 514/311

Primary Examiner—Leonard Schenkman

[57]  ABSTRACT

Phenylquinolinecarboxylic acids and derivatives thereof, such as 2-(2'-Fluoro-1,1'-biphenyl-4-yl)-6-fluoro-3-methyl-4-quinolinecarboxylic acid, or a sodium or potassium salt thereof, are useful for the treatment of skin and muco-epithelial diseases.

18 Claims, No Drawings

4-QUINOLINE CARBOXYLIC ACID DERIVATIVES USEFUL FOR TREATING SKIN AND MUCO-EPITHELIAL DISEASES

BACKGROUND OF THE INVENTION

1. Field of Invention

This invention relates to methods of treating skin and muco-epitfhelial diseases and more particularly to such method using phenyl quinoline carboxylic acids and derivatives thereof as a component of pharmaceutical compositions, more particularly of topical compositions.

2. Background

U.S. Pat. No. 4,680,299, granted July 14, 1987, to Hesson describes phenyl quinoline carboxylic acids and their derivatives as tumor inhibiting agents. Antitumor agents are typically administered internally by injection or by an oral dosage form.

Many diseases of the skin and muco-epithelia, such as psoriasis, are characterized by an inflammatory reaction in the underlying connective tissue and a hyperplasia (increased mitotic activity) of the overlying epithelia. Agents which suppress either or both the inflammatory and mitotic activity of the epithelia are effective in treating diseases of the skin.

The current treatment for skin and muco-epithelial diseases (i.e. psoriasis and chronic dermatitis is primarily based upon topical steroids. These are efficacious but have significant side effects such as skin atrophy, rosacea and adrenal suppression and thus are limited in their chronic usage.

A second common treatment for psoriasis is the use of coal tar or its derivatives. This treatment is unpleasant, not very effective and has potential for carcinogenesis. For moderate to severe cases of psoriasis, psoralens with UVA or drug such as methotrexate or cyclosporin A, whose side effects are kidney failure or liver toxicity, have been used with success.

No treatment is presently available which is at the same time effective, safe and cosmetically acceptable. Hence, a need exists for better treatment of skin and muco-epithelial diseases. The compounds described in U.S. Pat. No. 4,680,299 may offer improved efficacy over steroid and anti-metabolite therapy.

SUMMARY OF THE INVENTION

According to the present invention there is provided a method of treating a skin or muco-epithelia disease in a mammal comprising administering to the mammal an efficaceous amount of a compound having the formula:

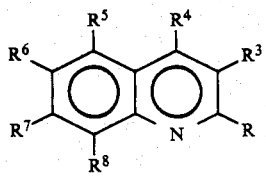

(I)

wherein

R is 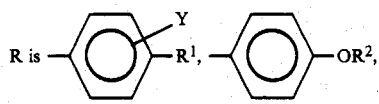

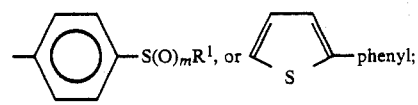

$R^1$ is $CH_3CH_2(CH_3)CH$, alkyl of 5–12 carbon atoms, cyclohexyl,

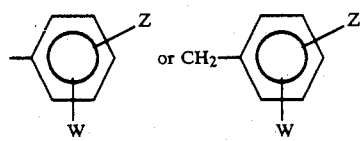

when R is

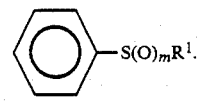

$R^1$ can be in addition alkyl of 3–4 carbon atoms;
$R^2$ is

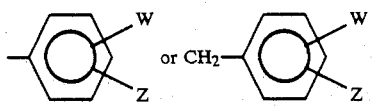

$R^3$ is H, alkoxy of 1–3 carbon atoms, or alkyl of 1–2 carbon atoms;
$R^4$ is $CO_2H$ or $CO_2R^{11}$;
$R^5$, $R^6$, $R^7$ and $R^9$ are independently H, F, Cl, Br, I, $CH_3$, $CF_3$, $SCH_3$ or $CH_2CH_3$, at least two of $R^5$, $R^6$, $R^7$ and $R^8$ being H;
$R^9$ and $R^{9A}$ are independently H or alkyl of 1 to 3 carbon atoms;
$R^{11}$ is $(CH_2)_{2-4}NR^9R^{9A}$;
W, Y and Z are independently H, F, Cl, Br, alkyl of 1–5 carbon atoms, $NO_2$, OH, $CF_3$ or $OCH_3$;
m is 0 or 1; or
a pharmaceutically suitable salt thereof;
with the following provisos:
(1) $R^5$, $R^6$ and $R^7$ cannot all be H;
(2) when $R^4$ is $CO_2CH_2CH_2N(CH_3)_2$, $R^6$ is $CH_2CH_3$, or $R^7$ is Cl, $R^1$ cannot be cyclohexyl;
(3) when $R^1$ is cyclohexyl and $R^3$ is H, $R^6$ must be Cl or F, but $R^6$ and $R^8$ cannot both be Cl; and
(4) when $R^6$ is $CH_3$, then $R^7$ cannot be Cl.

Also provided is a topical pharmaceutical composition consisting essentially of a carrier suitable for topical formulation and an efficaceous amount of one of the aforesaid compounds.

Additionally provided is the above-described method and topical composition wherein the abovedescribed compound is administered in combination with a steroid drug.

PREFERRED EMBODIMENT

Preferred compounds useful in the method and topical pharmaceutical composition have the formula:

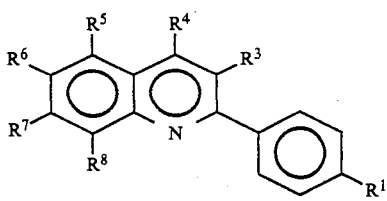

wherein
$R^1$ is cyclohexyl; phenyl; phenyl substituted with one halogen; alkyl of 1–5 carbon atoms or $CF_3$; phenoxy; or phenoxy substituted with one halogen or alkyl of 1–5 carbon atoms;

$R^3$ is H or alkyl of 1–2 carbon atoms;

$R^4$ is $CO_2H$, a sodium or potassium salt thereof; or $CO_2R^{11}$;

$R^5$ and $R^6$ are independently H, halogen, $CH_3$ or $CF_3$;

$R^7$ and $R^8$ are independently H or halogen;

$R^{11}$ is $(CH_2)_{2-4}NR^9R^{9A}$; and $R^9$ and $R^{9A}$ are independently alkyl of 1 to 3 carbon atoms, or a pharmaceutically suitable salt thereof; provided that $R^5$, $R^6$ and $R^7$ cannot all be H and that when $R^1$ is cyclohexyl and $R^3$ is H, $R^6$ must be Cl or F, but $R^6$ and $R^8$ cannot both be Cl, and when $R^6$ is $CH_3$, then $R^7$ cannot be Cl.

More preferred compounds useful in this invention have the formula:

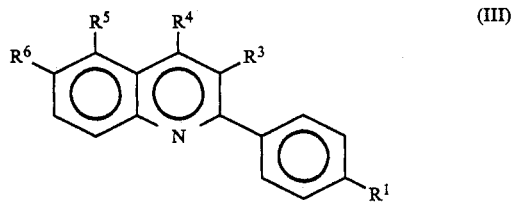

wherein
$R^1$ is cyclohexyl,

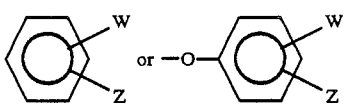

$R^3$ is H or alkyl of 1–2 carbon atoms;

$R^4$ is $CO_2H$, a sodium or potassium salt thereof, or $CO_2R^{11}$;

$R^5$ and $R^6$ are independently H, halogen or $CF_3$ provided that both $R^5$ and $R^6$ are not hydrogen;

$R^{11}$ is $(CH_2)_{2-4}NR^9R^{9A}$; and $R^9$ and $R^{9A}$ are independently alkyl of 1 to 3 carbon atoms, and W and Z are independently H, halogen, alkyl of 1–5 carbon atoms or $CF_3$; provided that when $R^1$ is phenyl or phenoxy, and $R^5$ is H, then $R^6$ cannot be Br; and that when $R^1$ is cyclohexyl and $R^3$ is H, $R^6$ must be Cl or F.

Specifically preferred compounds useful in this invention are:

(1) 2-(1,1'-biphenyl-4-yl)-6-fluoro-3-methyl-4-quinoline carboxylic acid, sodium or potassium salt (2) 6-fluoro-3-methyl-2-(4-phenoxyphenyl)-4-quinolione carboxylic acid, sodium or potassium salt (3) 2-(4'-bromo-1,1'-biphenyl-4-yl)-6-fluoro-3-methyl-4-quinole carboxylic acid, sodium or potassium salt (4) 2-(2'-fluoro-1,1'-biphenyl-4-yl)-6-fluoro-3-methyl-4-quinoline carboxylic acid, sodium or potassium salt (5) 2-(1,1'-biphenyl-4-yl)-5-chloro-3-methyl-4-quinoline carboxylic acid, sodium or potassium salt.

DETAILED DESCRIPTION OF THE INVENTION

The compounds useful in this invention are described in and prepared by methods set forth in U.S. Pat. No. 4,680,299, the discloure, synthesis and synthesis examples of which are hereby incorporated by reference.

The invention can be further understood by the following examples in which parts and percentages are by weight unless otherwise indicated; all temperatures are in degrees centigrade.

EXAMPLE 1

Part A 2-(1,1'-Biphenyl-4-yl)-5-chloro-3-methylquinoline-4-carboxylic acid

A mixture of 4-chloroisatin (7.28 g, 0.04 mol), [*J. Am. Chem. Soc.*, 1251 (1956)], 4-phenylpropiophenone (8.8 g, 0.04 mol), diethylamine (4 ml, 0.04 mol) and ethanol (200 ml) was stirred for a period of 18 hours at room temperature. The precipitated solids were collected by filtration, washed with ice-cold ethanol and air dried to yield the adduct (9.1 g, 58%) m.p. 209°–214° dec.

Part B

The above described adduct (9.1 g) was added to a mixture of tetrahydrofuran (200 ml), and concentrated HCl (200 ml) and heated at reflux for 24 hr. The reaction mixture was cooled, water (300 ml) was added and most of the tetrahydrofuran removed by evaporation in vacuo. The aqueous residue was cooled and the sticky solids collected by filtration. Trituration in 150 ml of boiling methanol yielded (4.8 g, 55%) m.p. 295°–297° dec.

$C_{23}H_{16}ClNO_2$ HRMS: 373.0869 Calcd, measured m/e 373.0814.

$^1$H NMR (DMSO-$d_6$): δ 8.5(m, 1H), 7.7–7.85(m, 7H), 7.35–7.55(m, 4H), 2.45(s, 3H).

Part C

Sodium 2-(1,1'-Biphenyl-4-yl)-5-chloro-3-methyl-quinolione-4-carboxylate

To a suspension of the above acid (3.7 g, 0.01 mol) in ethanol 100 ml, sodium hydroxide (1N, 10 ml, 0.01 mol) was added, and gently warmed. The clear solution was then filtered and evaporated to dryness to yield (4.0 g) m.p. 320°–330° dec.

EXAMPLE 2

Part A 2-(2-Fluoro-1,1'-biphenyl-4-yl)-6-fluoro-3-methyl-4-quinolione carboxylic acid 5-Fluoroisatin (72.6 g, 0.44 mole) and 4-(2-fluorophenyl)propiophenone (100 g, 0.44 mole) were suspended in 720 ml of ethanol and stirred mechanically as a solution of KOH (147.8 g, 2.64 mole) in 300 ml of water was added dropwise over 15 minutes. The reaction mixture was heated at reflux for 12 hours, cooled and the ethanol evaporated under reduced pressure. The resultiong solid was dissolved in water and washed with ethyl ether. The aqueous layer was cooled to 5° and acidified with glacial acetic acid. The resultiong precipitate was filtered, washed 2 times with 300 ml of ethyl ether and dried. Recrystallization from dimethylformamide and water gave 84 g of a white 2-(2'-Fluoro-1,1'-biphenyl-4-yl)-6-fluoro-3-methyl-4-quinoline carboxylic acid, m.p. 315°–317°.

Part B

Sodium 2-(2'-Fluoro-1,1'-biphenyl-4-yl)-6-fluoro-3-methylquinoline-4-carboxylate The compound of Part A (37.5 g, 0.10 mole) was suspended in 1,000 ml of ethanol and treated with 1N NaOH (100 ml, 0.10 mole). The mixture was warmed and stirred until clear; the ethanol and water were evaporated at reduced pressure to give 39.6 of the white solid sodium 2-(2'-fluoro-1,1'-biphenyl-4-yl)6-fluoro-3-methylquinoline-4-carboxylate, m.p. >360°.

UTILITY

Results of the biological tests described below establish that the compounds useful in this invention have the ability to inhibit skin hyperplasia induced by the repeated application of tetradecanoyl phorbol acetate (TPA) to mouse ears (Marks, et al., *Cancer Res.*, 36: 2626, 1976). As described, TPA is known to induce changes in murine skin which mimics many of the inflammatory and epithelial changes which occur in human skin diseases such as psoriasis.

TPA-INDUCED HYPERPROLIFERATION

CF-1 male mice (Charles River; weight: 20–25 g) were treated orally with compound prepared in 0.25% Methocel ® (Dow Chemical Co.) one hour prior to the application of 1 μg of TPA (in acetone) to the right ear with acetone only to the left ear. This treatment was repeated once a day for a total of 4 consecutrive days. On day 5, the animals were injected intraperitoneally with 2 mg/kg of vinblastine sulfate to arrest dividing cells in metaphase. Four hours later, the animals were sacrificed and the ears removed for histological processing. The histological slides were then examined in a light microscope and the metaphase figures per millimeter basement membrane counted. Ten mice were used per group. Results are shown in Tables 1 and 2.

TABLE 1

| Group | Dose (mg/kg) | TPA | Mitotic Activity Metaphase/mm BM* ± SEM** Figures |
| --- | --- | --- | --- |
| Negative Control | — | — | 1.3 ± 0.3 |
| Positive Control | — | + | 16.2 ± 1.1 |
| Methotrexate | 10.0 | — | 1.0 ± 0.2 |
|  | 10.0 | + | 9.0 ± 1.1 |
| Example 1 | 10.0 | — | 1.2 ± 0.4 |
|  | 10.0 | + | 5.1 ± 0.4 |
| Example 2 | 10.0 | — | 1.4 ± 0.2 |
|  | 10.0 | + | 8.4 ± 1.3 |

*mm BM = millimeters of basement membrane
**SEM = standard error of mean

The test results show that the compounds described herein effectively suppress the mitotic activity associated with mouse skin hyperplasia induced by TPA, indicative of efficacy in treating human skin and muco-epithelial diseases such as psoriasis (in all its forms), lichen planas, chronic eczema, icthyosis, pityriasis and chronic uticaria.

DOSAGE FORMS

The phenylquinolinecarboxylic acid derivatives useful in this invention can be administered to treat skin and muco-epithelial diseases such as psoriasis (in all its forms), lichen planas, chronic eczema, icthyosis, pityriasis and chronic uticaria. These compounds may be administered by any means that produces contact of the active agent with the agent's site of action in the body of a mammal. They can be administered by any conventional means available for use in conjunction with pharmaceuticals, either as individual therapeutic agents or in a combination of therapeutic agents, e.g., in combination with steroid drugs, particularly topical steroids such as Synalar (fluocinoloine acetonide), Lidex (fluocinolone), Westcort (hydrocortisone valerate), Valisone (betamethasone valeate), and Diprasone (betamethasoine dipropionate). They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler, or topically as an ointment, cream or lotion.

Gelatin capsules contaoin the active ingredient and powdered carriers, such as lactose, sucrose mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protected the tablet from atmosphere, or enteric coated for selective disintegration in the gastrointestinl tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Antioxidizing agents such as sodium bisulfite, sodium sulfite, or ascorbic acid either alone or combioned are suitable stabilizing agents. Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compound useful in this invention can be illustrated as follows:

CAPSULES

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

SOFT GELATIN CAPSULES

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by commonly used techniques.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

NASAL SPRAY

An aqueous solution is prepared such that each 1 milliliter contains 10 milligrams of active ingredient, 1.8 milligrams methylparaben, 0.2 milligrams propylparaben and 10 milligrams methylcellulose. The solution is dispensed into 1 milliliter vials.

LUNG INHALER

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

TOPICAL FORMULATIONS

An ointment for topical administration is prepared at 70° C. by addiong the active ingredient to a mixture of 48% by weight white petrolatum, 10% liquid petrolatum, 8% glycerol monostearate, 3% isopropyl myristate and 20% lanolin. After thorough mixing, a warm solution of methyl and propyl parabens in water containing sodium acetone bisulfite is added such that the final concentrations of each paraben is 0.15%, of water is 8% and of sodium acetone bisulfite is 0.5%. The mixture is stirred until it has reached room temperature.

A cream for topical administration is prepared at 75° C. by adding the active ingredient to a mixture of 1% sodium lauryl sulfate, 12% propylene glycol, 25% stearyl alcohol, 25% white petrolatum and 37% water. The mixture is stirred until it congeals.

A gel for topical administration is prepared at 70° C. by adding the active ingredient to a mixture of 0.75% Carbopol 940 (polycarbopol), 46.25% water, 3% emulsifier hydroxylated lanolin, 50% ethanol and, optionally, 1-2% diisopropanolamine. The mixture is stirred until it cools to room temperature.

What is claimed is:

1. A method of treating a skin or mucoepithelial disease in a mammal selected from the group consisting of psoriasis, lichen planas, chronic eczema, icthyosis, pityriasis and chronic uticaria comprising administering to the mammal an efficaceous amount of a compound having the formula:

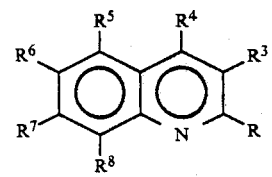

wherein

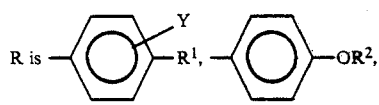

-continued

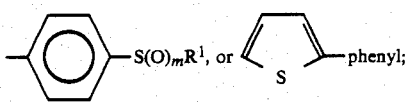

$R^1$ is $CH_3C_2(CH_3)CH$, alkyl of 5–12 carbon atoms, cyclohexyl,

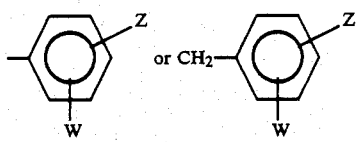

when R is

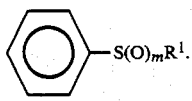

$R^1$ can be in addition alkyl of 3–4 carbon atoms; $R^2$ is

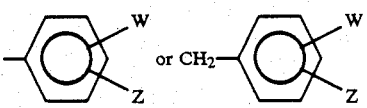

$R^3$ is H, alkoxy of 1–3 carbon atoms, or alkyl of 1–2 carbon atoms;
$R^4$ is $CO_2H$ or $CO_2R^{11}$;
$R^5$, $R^6$, $R^7$ and $R^8$ are independently H, F, Cl, Br, I, $CH_3$, $CF_3$, $SCH_3$ or $CH_2CH_3$, at least two of $R^5$, $R^6$, $R^7$ and $R^8$ being H;
$R^9$ and $R^{9A}$ are independently H or alkyl of 1 to 3 carbon atoms;
$R^{11}$ is $(CH_2)_{2-4}NR^9R^{9A}$;
W, Y and Z are independently H, F, Cl, Br, alkyl of 1–5 carbon atomns, $NO_2$, OH, $CF_3$ or $OCH_3$;
m is 0 or 1; or
a pharmaceutically suitable salt thereof; with the following provisos:
(1) $R^5$, $R^6$ and $R^7$ cannot all be H;
(2) when $R^4$ is $CO_2CH_2CH_2N(CH_3)_2$, $R^6$ is $CH_2CH_3$, or $R^7$ is Cl, $R^1$ cannot be cyclohexyl;
(3) when $R^1$ is cyclohexyl and $R^3$ is H, $R^6$ must be Cl or F, but $R^6$ and $R^8$ cannot both be Cl; and
(4) when $R^6$ is $CH_3$, then $R^7$ cannot be Cl.

2. The method of claim 1 wherein the compound has the formula:

(II)

wherein
$R^1$ is cyclohexyl; phenyl; phenyl substituted with one halogen; alkyl of 1–5 carbon atomsd or $CF_3$; phe-noxy; or phenoxy substituted with one halogen or alkyl of 1–5 carbon atoms;
$R^3$ is H or alkyl of 1–2 carbon atoms;
$R^4$ is $CO_2H$, a sodium or potassium salt thereof; or $CO^2R^{11}$;
$R^5$ and $R^6$ are independently H, halogen, $CH_3$ or $CF_3$;
$R^7$ and $R^8$ are independently H or halogen;
$R^{11}$ is $(CH_2)_{2-4}NR^9R^{9A}$; and
$R^9$ and $R^{9A}$ are independently alkyl of 1 to 3 carbon atoms, or a pharmaceutically suitable salt thereof;
provided that $R^5$, $R^6$ and $R^7$ cannot all be H and that when $R^1$ is cyclohexyl and $R^3$ is H, $R^6$ must be Cl or F, but $R^6$ and $R^8$ cannot both be Cl, and when $R^6$ is $CH_3$, then $R^7$ cannot be Cl.

3. The method of claim 1 wherein the compound has the formula:

(III)

wherein
$R^1$ is cyclohexyl, $R^3$ is H or alkyl of 1–2 carbon atoms;
$R^4$ is $CO_2H$, a sodium or potassium salt thereof, or $CO_2R^{11}$;
$R^5$ and $R^6$ are independently H, halogen or $CF_3$ provided that both $R^5$ and $R^6$ are not hydrogen;
$R^{11}$ is $(CH_2)_{2-4}NR^9R^{9A}$; and
$R^9$ and $R^{9A}$ are independently alkyl of 1 to 3 carbon atoms, and
W and Z are independently H, halogen, alkyl of 1–5 carbon atoms or $CF_3$;
provided that when $R^1$ is phenyl or phenoxy, and $R^5$ is H, then $R^6$ cannot be Br; and that when $R^1$ is cyclohexyl and $R^3$ is H, $R^6$ must be Cl or F.

4. The method of claim 1 wherein the compound is 2-(1,1'-biphenyl-4-yl)-6-fluoro-3-methyl-4-quinolinecarboxylic acid, sodium or potassium salt.

5. The method of claim 1 wherein the compound is 6-fluoro-3-methyl-2-(4-phenoxyphenyl)-4-quinolinecarboxylic acid, sodium or potassium salt.

6. The method of claim 1 wherein the compound is 2-(4'-bromo-1,1'-biphenyl-4-yl)-6-fluoro-3-methyl-4-quinolinecarboxylic acid, sodium or potassium salt.

7. The method of claim 1 wherein the compound is 2-(2'-fluoro-1,1'-biphenyl-4-yl)-6-fluoro-3-methyl-4-quinolinecarboxylic acid, sodium or potassium salt.

8. The method of claim 1 wherein the compound is 2-(1,1'-biphenyl-4-yl)-5-chloro-3-methyl-4-quinolinecarboxylic acid, sodium or potassium salt.

9. The method of claim 1 wherein the compound is administered in combination with a steroid drug.

10. A topical pharmaceutical composition in the form of an ointment, cream or gel consisting essentially of a carrier suitable for topical formulation and a topically efficaceous amount of a compound having the formula:

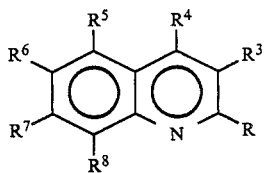

wherein

R is 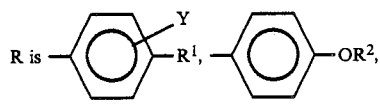

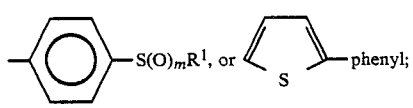

$R^1$ is cyclohexyl, when R is

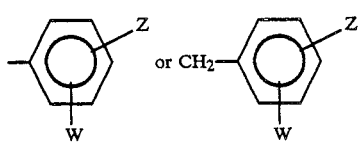

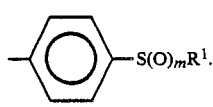

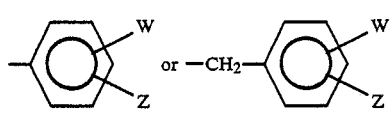

$R^1$ can be in addition alkyl of 3–4 carbon atoms;
$R^2$ is

R³ is H, alkoxy of 1–3 carbon atoms, or alkyl of 1–2 carbon atoms;
R⁴ is $CO_2H$ or $CO_2R^{11}$;
$R^5$, $R^6$, $R^7$ and $R^8$ are independently H, F, Cl, Br, I, $CH_3$, $CF_3$, $SCH_3$ or $CH_2CH_3$, at least two of $R^5$, $R^6$, $R^7$ and $R^8$ being H;
$R^9$ and $R^{9A}$ are independently H or alkyl of 1 to 3 carbon atoms;
$R^{11}$ is $(CH_2)_{2-4}NR^9R^{9A}$;
W, Y, and Z are independently H, F, Cl, Br, alkyl of 1–5 carbon atoms, $NO_2$, OH, $CF_3$ or $OCH_3$;
m is 0 or 1; or
a pharmaceutically suitable salt thereof; with the following provisos:
(1) when $R^4$ is $CO_2H$, $R^1$ or $R^2$ is phenyl and $R^5$, $R^7$ and $R^8$ are H, $R^6$ cannot be Br;
(2) $R^5$, $R^6$ and $R^7$ cannot all be H;

(3) when $R^1$ is $CO_2CH_2CH_2N(CH_3)_2$, $R^6$ is $CH_2CH_3$, or $R^7$ is Cl, $R^1$ cannot be cyclohexyl; and
(4) when $R^1$ is cyclohexyl and $R^3$ is H, $R^6$ must be Cl or F, but $R^6$ and $R^8$ cannot both be Cl; and
(5) when $R^6$ is $CH_3$, $R^7$ cannot be Cl.

11. The topical composition of claim 10 wherein the compound has the formula:

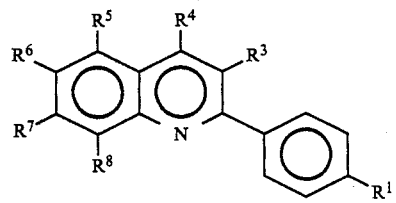

(II)

wherein
$R^1$ is cyclohexyl; phenyl; phenyl substituted with one halogen; alkyl of 1–5 carbon atoms $CF_3$; phenoxy; or phenoxy substituted with one halogen or alkyl of 1–5 carbon atoms;
$R^3$ is H or alkyl of 1–2 carbon atoms;
$R^4$ is $CO_2H$, a sodium or potassium salt thereof; or $CO^2R^{11}$;
$R^5$ and $R^6$ are independently H, halogen, $CH_3$ or $CF_3$;
$R^7$ and $R^8$ are independently H or halogen;
$R^{11}$ is $(CH_2)_{2-4}NR^9R^{9A}$; and
$R^9$ and $R^{9A}$ are independently alkyl of 1 to 3 carbon atoms, or a pharmaceutically suitable salt thereof;
provided that $R^5$, $R^6$ and $R^7$ cannot all be H and that when $R^1$ is cyclohexyl and $R^3$ is H, $R^6$ must be Cl or F, but $R^6$ and $R^8$ cannot both be Cl, and when $R^6$ is $CH_3$, then $R^7$ cannot be Cl.

12. The topical composition of claim 10 wherein the compound has the formula:

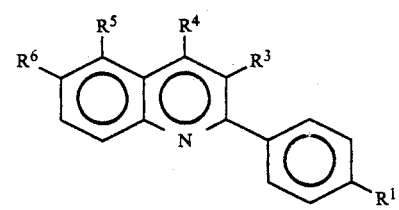

(III)

wherein
$R^1$ is cyclohexyl, $R^3$ is H or alkyl of 1–2 carbon atoms;
$R^4$ is $CO_2H$, a sodium or potassium salt thereof, or $CO_2R^{11}$;
$R^5$ and $R^6$ are independently H, halogen or $CF_3$ provided that both $R^5$ and $R^6$ are not hydrogen;
$R^{11}$ is $(CH_2)_{2-4}NR^9R^{9A}$; and
$R^9$ and $R^{9A}$ are independently alkyl of 1 to 3 carbon atoms, and
W and Z are independently H, halogen, alkyl of 1–5 carbon atoms or $CF_3$;

provided that when $R^1$ is phenyl or phenoxy, and $R^5$ is H, then $R^6$ cannot be Br; and that when $R^1$ is cyclohexyl and $R^3$ is H, $R^6$ must be Cl or F.

13. The topical composition of claim 10 wherein the compound is 2-(1,1'-biphenyl-4-yl-6-fluoro-3-methyl-4-quinoline-carboxylic acid, sodium or potassium salt.

14. The topical composition of claim 10 wherein the compound is 6-fluoro-3-methyl-2-(4-phenoxyphenyl)-4-quinoline-carboxylic acid, sodium or potassium salt.

15. The topical composition of claim 10 wherein the compound is 2-(4'-bromo-1,1'-biphenyl-4-yl)-6-fluoro-3-methyl-4-quinoline-carboxylic acid, sodium or potassium salt.

16. The topical composition of claim 10 wherein the compound is 2-(2'-fluoro-1,1'-biphenyl-4-yl)-6-fluoro-3-methyl-4-quinoline-carboxylic acid, sodium or potassium salt.

17. The topical composition of claim 10 wherein the compound is 2-(1,1'-biphenyl-4-yl)-5-chloro-3-methyl-4-quinolinecarboxylic acid, sodium or potassium salt.

18. The topical composition of claim 10 wherein the compound is present in combination with a steroid drug.

* * * * *